United States Patent [19]

Hoffmann et al.

[11] 4,001,344

[45] Jan. 4, 1977

[54] CATALYST FOR PARTIAL HYDROGENATION

[75] Inventors: Herwig Hoffmann, Frankenthal; Guenther Boettger, Bad Duerkheim; Karl Baer, Weinheim; Harro Wache, Fussgoenheim; Heinz Graefje, Ludwigshafen; Wolfgang Koernig, Dossenheim, all of Germany

[73] Assignee: BASF Aktiengesellschaft, Ludwigshafen (Rhine), Germany

[22] Filed: June 30, 1975

[21] Appl. No.: 591,834

[30] Foreign Application Priority Data

July 3, 1974 Germany .......................... 2431929

[52] U.S. Cl. .......................... 260/635 M; 252/439; 252/473
[51] Int. Cl.² .......................................... C07C 33/02
[58] Field of Search .......................... 252/439, 473; 260/635 M

[56] References Cited

UNITED STATES PATENTS

| | | | |
|---|---|---|---|
| 2,662,861 | 12/1953 | Riblett et al. | 252/473 X |
| 3,407,227 | 10/1968 | Beck et al. | 260/635 M X |
| 3,450,776 | 6/1969 | Di Cio et al. | 260/635 M X |
| 3,644,486 | 2/1972 | Boldt et al. | 252/439 X |
| 3,755,198 | 8/1973 | Stratenus | 252/473 X |

*Primary Examiner*—Patrick P. Garvin
*Attorney, Agent, or Firm*—Johnston, Keil, Thompson & Shurtleff

[57] ABSTRACT

A palladium catalyst for the maufacture of butene-2-diol-1,4 from technical butynediol obtained by reacting acetylene and formaldehyde by the Reppe method in contact with copper catalysts and not specially purified contains (in addition to palladium) both zinc and cadmium, or either zinc or cadmium together with bismuth or tellurium.

10 Claims, No Drawings

CATALYST FOR PARTIAL HYDROGENATION

Partial hydrogenation of acetylene compounds such as are produced by so-called Reppe ethynylation leads to olefinically unsaturated compounds.

This is described, inter alia, in U.K. Patent 871,804, which also contains other details of this process, for which reason said patent specification is incorporated herein by reference.

Said process is particularly important for the manufacture of butene-2-diol-1,4 from butynediol which is in turn available from acetylene and formaldehyde. Butene-2-diol-1,4 is an important intermediate in the production of plant protection agents and pharmaceuticals.

In one known process, the hydrogenation is carried out in aqueous or alcoholic solution in contact with a palladium-containing catalyst, of which the selectivity is improved by the addition of compounds of metals in group IIa or group IIIa of the Periodic Table.

The process of partial hydrogenation gives, at least in the case of butynediol, satisfactory results only when pure compounds are used as starting materials. Technical grades of butynediol containing as impurities for example propargyl alcohol, formaldehyde, formates and residues of the previously used catalyst, particularly silicic acid and copper, have been found to form considerable quantities of resinified residues, in some cases up to 30%.

It is an object of the present invention to provide novel, efficient and selective catalysts which are less affected by the presence of impurities in technical butynediol and which effect selective hydrogenation of the triple bond to a double bond.

We have found a novel catalyst which contains palladium and a metal of group IIb of the Periodic Table on a support.

According to the invention, the catalyst contains, in addition to palladium, one of the elements zinc and cadmium and at least one of the elements bismuth and tellurium, or both zinc and cadmium. Obviously, it may also contain both zinc and cadmium in addition to bismuth and/or tellurium.

A particularly advantageous support is alumina or pumice, particularly γ-aluminum oxide or a modified aluminum oxide such as is known under the trade name Catapal and is prepared from organo-aluminum compounds, or pumice, particularly purified Italian pumice.

The invention is particularly suitable for the hydrogenation of technical butynediol to butenediol in aqueous solution, this being an industrially very important process.

By technical butynediol we mean butyne-2-diol-1,4 which has been prepared by reacting pure or technical acetylene and formaldehyde in aqueous solution, for example by the process of German Patent 725,326 or German Published Application 2,040,501, and which has not been specially purified. Such technical butynediol generally contains varying quantities of formaldehyde and propargyl aldehyde and is in the form of an approximately 30% aqueous solution. It also contains varying amounts of the previously used catalyst (copper, silicate) and also sodium formate and methanol. Under hydrogenation conditions, these impurities cause, inter alia, the formation of 4-hydroxybutyraldehyde from butenediol, which compound causes resinification.

Particularly suitable butynediol is generally obtained from technical butynediol by multiple distillation.

Whereas conventional catalysts, for example catalysts containing only palladium, palladium/zinc, palladium/manganese dioxide, palladium/lead or palladium/vanadium on a support, frequently form more than 25% and in some cases as much as 40% of residues in the manufacture of butenediol, the catalysts of the invention make it possible to obtain butenediol from technical butynediol at a much lower rate of residue formation, generally less than 10%.

It will be appreciated that the catalyst is also highly suited for the production of butene-2-diol-1,4 from pure butynediol, particularly under large-scale operating conditions.

The catalysts of the invention generally contain from about 0.05 to 2% and in particular from 0.2 to 0.7% of palladium and from about 0.05 to 1% and in particular from 0.1 to 0.3% of zinc and/or cadmium. If only zinc or cadmium is present, they also contain from about 0.05 to 1% and in particular from 0.1 to 0.3% of bismuth or tellurium, by weight. Zinc-containing catalysts are preferred.

The catalysts are generally used in the form of a suspension in which the average particle size is, say, from 0.02 to 1 and in particular from 0.05 to 0.35 mm in diameter. It will be appreciated that the catalysts may also be used in the form of a fixed bed.

In general, the reaction conditions employed in the manufacture of butenediol do not differ from the prior art conditions; for example, a hydrogen pressure of from atmospheric to about 16 bars is used, the upper limit generally being determined merely by the specifications laid down by the equipment manufacturers and not by chemical phenomena. The reaction temperature is generally from 30° to 80° C and in particular from 60° to 75° C.

EXAMPLE 1

850 g of γ-Al$_2$O$_3$ having a particle size of 0.05 to 0.5 mm are thoroughly mixed with 38.95 g of an 11% palladium nitrate solution containing 4.28 g of Pd and also with 3.82 g of zinc nitrate (zinc content 0.85 g), 2 g of cadmium nitrate (cadmium content 0.85 g) and 600 ml of water. The mixture is then dried for 16 hours at 120° C. The catalyst is then heated for 6 hours at 520° C. After this heat treatment, the catalyst contains 0.48% of Pd, 0.1% of Cd and 0.09% of Zn.

60 kg of 33% technical aqueous 2-butyne-1,4-diol solution are hydrogenated in the presence of 400 g of the above catalyst at 72° C and at a hydrogen pressure of 12.5 bars. In addition to 18.0 kg of 2-butene-1,4-diol, equivalent to a yield of 89%, there are produced 2.2 kg or 11% by weight of residue.

EXAMPLE 2

850 g of γ-Al$_2$O$_3$ having a particle size of from 0.08 to 0.4 mm are thoroughly mixed with 38.95 g of an 11% palladium nitrate solution containing 4.289 g of Pd and with 2 g of bismuth nitrate (bismuth content 0.9 g), 3.82 g of zinc nitrate (zinc content 0.85 g) and 570 ml of water. The mixture is then dried for 16 hours at 120° C. The catalyst is then heated for 6 hours at 520° C. After this heat treatment, the catalyst contains 0.5% of Pd, 0.1% of Bi and 0.1% of Zn.

60 kg of 33% technical aqueous 2-butyne-1,4-diol solution are hydrogenated in the presence of 44 g of the above catalyst at 65° C and a hydrogen pressure of 4 bars. In addition to 18.7 kg of 2-butyne-1,4-diol, equivalent to a yield of 92.5%, there are produced 1.5 kg or 7.5% by weight of residue.

EXAMPLE 3

850 g of $\gamma$-Al$_2$O$_3$ having a particle size of from 0.05 to 0.5 mm are thoroughly mixed with 38.95 g of an 11% palladium nitrate solution containing 4.284 g of palladium and with 3.82 g of zinc nitrate (Zn content 0.85 g), an aqueous solution of telluric acid having a tellurium content of 0.85 g and 600 ml of water. This mixture is then dried for 16 hours at 120° C. The catalyst is then heated for 6 hours at 510° C. After this heat treatment, the catalyst contains 0.5% of palladium, 0.1% of tellurium and 0.1% of zinc.

60 kg of 35% technical aqueous 2-butyne-1,4-diol solution are hydrogenated in the presence of 400 g of the above catalyst at 68° C and a hydrogen pressure of 6 bars. In addition to 17.8 kg of 2-butene-1,4-diol, equivalent to a yield of 88%, there are produced 2.4 kg or 12% by weight of residue.

COMPARATIVE EXAMPLE 1

850 g of $\gamma$-Al$_2$O$_3$ having a particle size of from 0.05 to 0.5 mm are mixed with 39 g of an 11% palladium nitrate solution and 560 ml of water. The mixture is then dried, drying being completed at 120° C for 16 hours. The catalyst is then heated at 520° C. Its final content of palladium is 0.5% by weight.

60 kg of 33% aqueous technical 2-butyne-1,4-diol solution are hydrogenated with 400 g of the above catalyst at 65° C and a hydrogen pressure of 6 atmospheres gage. There are obtained 11.9 kg of 2-butene-1,4-diol, equivalent to a yield of 58.8%. In addition, there are produced 8.3 kg of 41.2% by weight of residue.

COMPARATIVE EXAMPLE 2

850 g of $\gamma$-Al$_2$O$_3$ are treated as described above but with the addition of zinc nitrate to give a catalyst having a palladium content of 0.5% and a zinc content of 0.2%, by weight.

60 kg of 33% aqueous technical 2-butyne-1,4-diol solution are hydrogenated with 400 g of this catalyst at 65° C and a hydrogen pressure of 6.5 bars. There are obtained 10.85 kg of 2-butene-1,4-diol, equivalent to a yield of 53.7% of theory. In addition, there are produced 9.35 kg or 46.3% by weight of residue.

We claim:

1. A process for the manufacture of butene-2-diol-1,4 by hydrogenation of butynediol in aqueous solution in the presence of a supported catalyst which comprises: contacting said butynediol with a catalyst, said catalyst comprising from 0.05 to 2 percent palladium and from 0.05 to 1 percent of zinc and cadmium.

2. A process for the manufacture of butene-2-diol-1,4 by hydrogenation of butynediol in aqueous solution in the presence of a supported catalyst which comprises: contacting said butynediol with a catalyst, said catalyst comprising from 0.05 to 2 percent palladium, from 0.05 to 1 percent zinc or cadmium, and from 0.05 to 1 percent of bismuth and/or tellurium.

3. A process as set forth in claim 1 wherein said support is alumina or pumice.

4. A process as set forth in claim 2 wherein said support is alumina or pumice.

5. A process as set forth in claim 1 wherein said catalyst comprises from 0.2 to 0.7 percent palladium, and from 0.1 to 0.3 percent zinc and cadmium.

6. A process as set forth in claim 2 wherein said catalyst comprises from 0.2 to 0.7 percent palladium, from 0.1 to 0.3 percent of zinc and cadmium, and from 0.1 to 0.3 percent of bismuth and/or tellurium.

7. A process as set forth in claim 1 wherein said catalyst has been prepared by mixing said support with an aqueous solution of the nitrates of palladium, zinc, and cadmium, and heat treating the mixture.

8. A process as set forth in claim 2 wherein said catalyst has been prepared by mixing said support with an aqueous solution of the nitrates of palladium, zinc, cadmium, and bismuth and/or telluric acid, and heat treating the mixture.

9. A process as set forth in claim 1 wherein said hydrogenation occurs at a hydrogen pressure of from atmospheric to about 16 bars and a temperature of from 30° to 80° C.

10. A process as set forth in claim 2 wherein said hydrogenation occurs at a hydrogen pressure of from atmospheric to about 16 bars and a temperature of from 30° to 80° C.

* * * * *